United States Patent [19]

Weirauch et al.

[11] 4,299,948
[45] Nov. 10, 1981

[54] MACROCYCLIC POLYCARBONATES

[75] Inventors: Kurt Weirauch, Bergisch Gladbach; Alfred Horbach, Krefeld; Hugo Vernaleken, Walsrode, all of Fed. Rep. of Germany

[73] Assignee: Bayer Aktiengesellschaft, Leverkusen, Fed. Rep. of Germany

[21] Appl. No.: 97,272

[22] Filed: Nov. 26, 1979

[30] Foreign Application Priority Data

Sep. 14, 1979 [DE] Fed. Rep. of Germany ....... 2937332

[51] Int. Cl.³ .............................................. C08G 63/62
[52] U.S. Cl. .................................. 528/171; 528/174; 528/196; 528/199; 528/204
[58] Field of Search ............... 528/171, 174, 196, 199, 528/204

[56] References Cited

U.S. PATENT DOCUMENTS

| | | | |
|---|---|---|---|
| 3,220,975 | 11/1965 | Fox | 260/33.8 R |
| 3,221,025 | 11/1965 | Prochaska | 528/196 |
| 3,275,601 | 9/1966 | Schnell et al. | 260/47 |
| 3,386,954 | 6/1968 | Schnell et al. | 260/47 |
| 4,129,574 | 12/1978 | Hallgren | 260/340.2 |
| 4,139,687 | 2/1979 | Sannes | 526/1 |
| 4,197,394 | 4/1980 | Hallgren | 528/198 |

OTHER PUBLICATIONS

Staudinger et al., *Makromol. Chem.* 57, 1962, pp. 1–11.

*Primary Examiner*—Maurice J. Welsh

*Attorney, Agent, or Firm*—Gene Harsh; Lawrence S. Pope; Aron Preis

[57] ABSTRACT

The subject of the instant invention are polycarbonates based on diphenols of the formula I

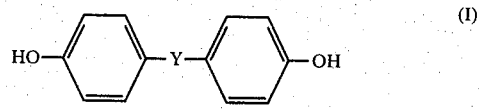
(I)

wherein
Y is a single bond, an elkylene- or alkylidene-radical with 1 to 7 carbon atoms, a cycloalkylene- or cycloalkylidene-radical with 5 to 12 carbon atoms,

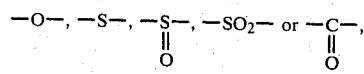

which have weight average molecular weights ($M_{LS}$) measured by light scattering of at least 15 000 and which are characterized in having an average of zero to 1.5 mols, preferably 0.3 to 1.0 mols and especially 0.3 to 0.8 mols endgroups per mol polycarbonate.

The subject of instant invention is also a process for preparing these polycarbonates according to the interfacial polycondensation method, the polycarbonates thus obtained and the use of the polycarbonates according instant invention for the preparation of compounds and films.

5 Claims, No Drawings

MACROCYCLIC POLYCARBONATES

The subject of the present invention are polycarbonates based on diphenols of the formula (I)

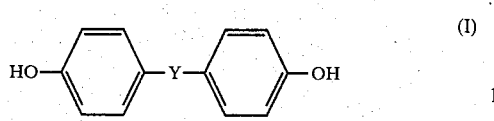

in which
Y denotes a single bond, an alkylene or alkylidene radical with 1–7 C atoms, a cycloalkylene or cycloalkylidene radical with 5–12 C atoms, —O—, —S—,

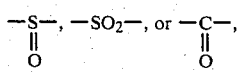

which have weight average molecular weights (MLS measured by light scattering) of at least 15,000 and which are characterised in that the polycarbonates contain on the average of 0 to 1.5 mols, preferably 0.3–1.0 mols, in particular 0.3–0.8 mols end groups per mol polycarbonate.

In particular the polycarbonates according to the invention have weight average molecular weights (MLS measured by light scattering) from 15.000 to 135,000, preferably from 20.000 to 100.000.

The subject of the present invention is also a process for the production of the polycarbonates according to the invention according to the method of interfacial process using amine catalysis, but without using chain stoppers, characterised in that solutions containing bischlorocarboxylic, acid esters of diphenols of formula (I) in inert organic solvents are reacted with aqueous, amine catalyst solutions containing optionally up to 50 mol %, based on the total molar amount of diphenols of formula (I) to be used, of alkali metal diphenolates of diphenols of formula (I) and/or free diphenols of formula (I), at pH values ≧9 and using 0.05 to 30 mols, preferably from 0.7 to 20 mols, and in particular from 2 to 10 mols, per mol of the total molar amount of the diphenols of formula (I) to be used in each case, of amine catalyst.

Included in the total molar amount of diphenols of formula (I) to be used in each case are, apart from the free diphenols as such, also those which are used, in each case, in the form of bischlorocarboxylic acid esters and diphenolates.

Instead of, or in addition to the bischlorocarboxylic acid esters, chlorocarboxylic-acid-ester-containing prephosgenates of diphenols of formula (I) are used for the polycarbonate production according to the invention.

Included in the subject of the invention are also the polycarbonates obtained according to the invention as well as the use of the polycarbonates according to the invention for the production of mouldings and films.

Polycarbonates based on aromatic dihydroxy compounds are above all known through the papers by H. Schnell, Chemistry and Physics of Polycarbonates, (Interscience Publishers, New York, 1964). The polycarbonate based on 2,2-bis(4-hydroxyphenyl)-propane (bisphenol A) has in particular, gained significance on a wide industrial scale, this polycarbonate being used in many fields of application, on account of its outstanding combination of properties.

Three technical processes are essentially known for the production of the aromatic polycarbonates:

1. The process of melt reesterification of diphenols with diaryl carbonates.
2. The solvent process in the homogeneous, organic phase, in which the diphenol is reacted with phosgene, adding at least equimolar amounts of an amine, for example, pyridine.
3. The interfacial process, in which an aqueous alkaline solution of diphenol is reacted with phosgene or bischlorocarboxylic acid esters of diphenols, in the presence of a second water-immiscible organic polycarbonate-dissolving phase, adding catalytic amounts of a tertiary amine or a quarternary ammonium compound.

The polycarbonates obtainable according to the known processes consist essentially of linear molecules, i.e. the molecules contain practically 2 end groups.

Cyclic low-molecular carbonates are known from literature (see, for example, Makromol. Chem. (Macromolecular Chemistry) 57, pg. 1–11, 1962), which are produced by the reaction of diphenols with bischlorocarboxylic acid esters of diphenols in homogeneous phase. These cyclic carbonates do not however have thermoplastic properties. Although they can be converted into high-molecular polycarbonates by heating, according to U.S. Pat. No. 3,386,954, the molecules which are formed by doing so are linear and have essentially 2 end groups per molecule.

It has now surprisingly been found that it is also possible to produce polycarbonates whose molecules on average contain far below 2 end groups per molecule. Under certain conditions, which will be described in more detail below polycarbonates can even be produced whose molecules no longer contain any end groups and thus possess a macrocyclic structure. By varying the reaction conditions, polycarbonates containing on the average between 0 and 1.5 end groups per molecule can, if required, be produced.

1.0 end groups per molecule means that a mixture of 50 mol % of linear polycarbonate molecules and 50 mol % of cyclic polycarbonate molecules are present.

One process for the production of the polycarbonates according to the invention comprises the following: an aqueous catalyst solution, preferably an approximately 1% strength aqueous triethylamine solution, is initially introduced, and an approximately 5 to 10% by weight solution of diphenol bischlorocarboxylic acid ester in an inert organic solvent (for example, methylene chloride) is added while stirring vigorously. The temperature during this procedure should be in the range of 0°–40° C. If the reaction takes place too exothermically, it is recommendable to reduce the rate of addition of the organic phase and/or to use lower concentrations of the bischlorocarboxylic acid ester in the inert solvent. In order to obtain complete conversion it is recommendable to continue stirring for 30 minutes following the addition of the organic phase.

In this way polycarbonates essentially free of end groups are obtained. Control of the molecular weight is conducted by varying the process conditions. The quantity of amines and the reaction temperature have the greatest effect on the molecular weight. By lowering the reaction temperature to 0° C., using the same quantity of amine, higher molecular weights are obtained in comparison with a reaction temperature of 25° C. At amine quantities of over 10 mols, based on 1 mol of the total molar amount to be used of diphenol of formula (I), polymers with lower molecular weights are produced; at amine quantities of <2 mols, based on 1 mol of the total molar amount to be used of diphenol of the formula (I), products with higher molecular weights are formed.

The process can, however, also be conducted in such a way that in the aqueous phase up to 50 mol %, based on the total molar amount to be used of diphenol of the formula (I), of diphenol as such and/or in the form of its alkali metal salt is initially introduced together with the catalyst and is reacted with the bischlorocarboxylic acid ester, as described above.

The use of high amine concentrations (10–200 mol %, based on the bisphenols and/or bischlorocarboxylic acid esters to be used) for the production of polycarbonates according to the interfacial process, at least 50 mol % of which consist of bisphenols substituted by tetraalkyl in the ortho position, is also described in the German Offenlegungsschrifts DE-AS No. 2,063,050 and DE-OS No. 2,211,957. The polycarbonates produced according to this process consist, however, essentially of linear molecules.

The polycarbonate production according to the interfacial process without the use of chain stoppers and with amine catalysis is also described in U.S. Pat. No. 3,275,601 and U.S. Pat. No. 3,220,975; however, the special combination of the production according to the invention, using chlorocarboxylic acid esters of the formula (I) and/or their chlorocarboxylic-acid-ester-containing pre-phosgenates, with the amine amounts according to the invention, is not mentioned in these patents, nor is it prompted by them.

Suitable catalysts are the aliphatic or cycloaliphatic tertiary amines commonly used for the interfacial process for polycarbonate production, such as for example triethylamine, tri-n-butylamine, N-ethylpiperidine or N-ethylmorpholine.

Suitable inert organic solvents for the solutions containing bischlorocarboxylic acid esters are, for example, methylene chloride and chlorobenzene, as well as mixtures thereof.

The process according to the invention can be conducted within the temperature range of between 0° and 40° C.

The concentration of the diphenol-bischlorocarboxylic acid ester in the inert solvent is approximately 0.5–70% by weight, preferably 3–10% by weight, based on the total weight of bischlorocarboxylic acid ester and solvent.

The concentration of the diphenol, optionally also used, including the diphenolate in the aqueous solution, is 0.5–10% by weight, preferably 1–4% by weight, based on the total weight of diphenol, diphenolate and aqueous alkaline amine solution.

According to the process of the invention bischlorocarboxylic acid esters of diphenols of formula (I) can be used.

Suitable diphenols of formula (I) are, for example, bis-(4-hydroxy-phenyl)-alkanes, bis-(4-hydroxyphenyl)-cycloalkanes, bis-(4-hydroxyphenyl)-sulphides, bis-(4-hydroxyphenyl)-ethers, bis-(4-hydroxyphenyl)-sulphoxides, bis-(4-hydroxyphenyl)-sulphones and bis-(4-hydroxy-phenyl)-ketones.

These and further suitable diphenols of formula (I) are described, for example, in the U.S. Pat. Nos. 3,028,365, 2,999,835, 3,148,172, 3,217,368, 2,991,273, 3,271,367, 3,280,078, 3,014,891 and 2,999,846 and in the monograph "H. Schnell, Chemistry and Physics of Polycarbonates," Interscience Publishers, New York, 1964.

Preferred diphenols are, for example: 2,2-bis-(4-hydroxyphenyl)-propane, 1,1-bis-(4-hydroxyphenyl)-cyclohexane and bis-(4-hydroxyphenyl)-sulphone.

The corresponding bischlorocarboxylic acid esters are produced according to known processes, e.g. from phosgene and diphenol in the presence of N,N'-dimethylaniline. The production of the bisphenol A bis-chlorocarboxylic acid ester is described in the experimental section.

The chlorocarboxylic-acid-ester-containing pre-phosgenates of the diphenols of formula (I), to be used according to the invention, are also obtainable according to known processes.

The high-molecular polycarbonates obtainable according to the invention exhibit, in particular, relative solution viscosities of 1.15 to 1.80, measured in methylene chloride at 25° C. in a concentration of 0.5 g/l and weight average of 15,000 to 135,000 molecular weights, measured by light scattering (MLS). In contrast to this, linear polycarbonates have weight average molecular weights of 13,000 to 80.000 at comparable solution viscosities.

ANALYTIC SECTION

Determination of the end groups of aromatic polycarbonates

1. Possible end groups in the polycarbonates according to the invention

In the polycarbonates concerned the following end groups are possible:

1.1 bisphenol A not completely converted difunctionally produces a content of free phenolic OH end groups, 1.2 chloroformic acid ester groups which are not completely converted produce a content of saponifiable chlorine 1.3 monofunctional phenols as chain stoppers (see comparative example)

1.4 the polycarbonates produced contain nitrogen incorporated in end groups, in amounts of 30–250 ppm. IR compensation spectra with nitrogen-free polycarbonates show a band at 1705 cm$^{-1}$, which can be associated with the diethylcarbamate group. The formation of such groups, which are end groups, takes place by the reaction of chloroformic acid ester groups with the diethylamine (approx. 0.5%) being as an impurity in the catalyst triethylamine.

If the polycarbonate is not sufficiently purified the nitrogen content is further increased by amine bonded by adsorption. Owing to the low content of nitrogen in the products it was considered collectively as an end group, for the purpose of simplification. Any errors which may be caused by this only increase the end group content very slightly and tend rather to cause an excess of end groups to be shown in the analysis of the end groups than give an appearance of macrocycles.

1.5 Further end groups could not be detected in the polymers in question—even when using highly-sensitive analysis methods, i.e. the reactions producing the following end groups do not occur, under suitable conditions:

(a) splitting of bisphenol A in the isopropylidene group to give phenyl carbonate and p-isoproylphenyl carbonate end groups, (b) CO₂-formation from chlorocarboxylic acid ester groups with the formation of 4-(2-(4-chlorophenyl)-isopropyl)-phenylcarbonate end groups and (c) Kolbe rearrangement with the formation of carboxyl end groups.

2. Methods of quantitative end group analysis 2.1 Phenolic OH end groups

Phenolic OH end groups are appropriately detected according to the photometric method described by Horbach et al.[1]), following reaction with TiCl₄. Detection limit: 10 ppm 1. A Horbach, U. Veiel, H. Wunderlich, Die Makromol. Chemie 83, 215 (1965)

2.2 Chloroformic acid ester end groups

The amount of chloroformic acid ester end groups can be determined by detecting the chlorine saponifiable with aniline, with the aid of argentometric titration[2]).

2. Argentometric processes: in W. Fresenius, G. Jander, Handbuch der analyt. Chemie (Manual of analytic chemistry), Part 3, Quantitative Bestimmungs- und Trennungsmethoden (Quantitative detection and separation methods), Vol. VII a β, Elemente der siebenten Hauptgruppe II Springer Publishers, Berlin 1967, pg. 96, et seq., The chlorine present in inorganic form as chloride (in the case of samples not well washed) must be—since it is included in the detection—determined separately and deducted. Detection limit of the saponifiable chlorine: 2 ppm.

2.3 Monofunctional phenols (see comparative example)

The following method of high pressure liquid chromatography can be used for determining the content of monophenols:

After the polycarbonate has been completely saponified and the obtained solution has been acidified the solution is examined directly by means of chromatograph HP 1084 B. The chromatographical conditions for, for example, phenol in the form of monophenol are: 10 cm column, with 5 mm φ, filled with Lichrosorb C8 (Merck), particle size 5μ, flow speed 1 ml/min, isocratically: 70% water, 30% methanol (V/V) UV detector 254 nm, 0.1 E, method of calculation: external standard.

This method is at present the most exact method of examination with the lowest detection limit and is therefore especially suitable for these polycarbonate samples according to the invention. (Detection limit: 10 ppm).

2.4 Nitrogen-containing end groups

Nitrogen-containing end groups can appropriately be detected quantitatively by nitrogen analysis according to Kjeldahl using photometric detection[3]). Detection limit: 10 ppm nitrogen.

3. "The Kjeldahl Method for Organic Nitrogen" R. B. Bradstreet Academic Press, New York and London, 1965.

3. Absolute determination of the number average molecular weight

For the determination of the number average molecular weight osmometric methods are appropriately used. It must be pointed out that these methods sometimes give excessive molecular weights if used uncritically.

(a) Membrane-osmometric determinations require a membrane which is impermeable to the solute, but easily permeable to the solvent. Since macromolecular substances, e.g. the polycarbonate, have a broad molecular weight distribution, it is to be expected that the low-molecular portion is partly able to permeate the membrane and escape the detection. The result is the detection of too low an osmotic pressure and therefore too high a molecular weight.

(b) Vapour pressure osmometric determinations detect—since it can be assumed that the polycarbonate has a negligible vapour pressure—the total amount of macromolecular substances dissolved in the solvent, including the low-molecular portion. Since, for a better determination of the properties to be measured comparatively high concentrations of the polycarbonate are used, it must be proven, for example by measuring in 2 thermodynamically different solvents, that the results of the molecular weight determinations are not influenced by association effects, i.e. that excessive $M_n$ values are found.

The following measuring procedure has proven to be advantageous, in the case of polycarbonates, for the determination of correct molecular weight values:

For $M_n$ values > 5,000 the molecular weight determination by means of membrane-osmosis is the most suitable method. Ultrazella filters are suitable as the membranes, which, after appropriate additional shrinkage, allow recording of the exact standardizing kinetics of the osmometric pressure, so that any low-molecular contents present are also detected by extrapolation.

For $M_n$ values between 2,000 and 5,000, vapour pressure osmometric determinations can additionally be conducted with good exactness. For $M_n$ values < 2,000 only vapour pressure osmometric determinations in 2 different solvents should be used. If the determinations according to 2 methods or in 2 different solvents comply with each other, the measurement can be considered as being correct and free from association effects of the solute in the solvent.

4. Calculation of the molecular weight from the end groups and calculation of the number of end groups The molecular weight $M_E$ for linear molecules can be calculated from the total amount of all end groups. The following applies in the case of the polycarbonate according to the invention:

$$M_E = \frac{X \cdot 100}{\frac{\% \text{ Phenol}}{94} + \frac{\% \text{ OH}}{17,0} + \frac{\% \text{ Cl}}{35,5} + \frac{\% \text{ N}}{14,0}}$$

X = number of end groups per molecule (2 in the case of linear molecules)

If the equation is rewritten and $M_E$ is replaced by the osmometrically determined molecular weight, the number of end groups, X, per molecule is obtained according to the following equation:

$$X = \frac{M_{OS}\left(\frac{\% \text{ Phenol}}{94} + \frac{\% \text{ OH}}{17,0} + \frac{\% \text{ Cl}}{35,5} + \frac{\% \text{ N}}{14,0}\right)}{100}$$

5. Examples of results of the analyses using Comparative Example (Example 1) and Example 3

| Preparation | % OH[1] | sap. Cl[2] | % N[3] | % phenyl[4] | $M_E$[5] | $\eta_{rel}$[6] | $M_\eta$[7] | $M_{os}$[8] | x[9] |
|---|---|---|---|---|---|---|---|---|---|
| Comparative example | 0.05 | 2 ppm | 0.003 | 1.05 | 14,000 | 1.270 | 28,000 | 13,800 | 1.97 |

-continued

| Preparation | % OH[1] | sap. Cl[2] | % N[3] | % phenyl[4] | $M_E$[5] | $\eta_{rel}$[6] | $M_\eta$[7] | $M_{os}$[8] | x[9] |
|---|---|---|---|---|---|---|---|---|---|
| Example 3 | 0.01 | 9 ppm | 0.013 | — | 127,000 | 1.291 | 24,700 | 13,800 | 0.22 |

[1] phenolic OH end groups determined according to paragraph 2.1
[2] saponifiable Cl determined according to paragraph 2.2
[3] nitrogen as end group determined according to paragraph 2.4
[4] phenyl end groups determined according to paragraph 2.3
[5] $M_E$ defined according to paragraph 4.
[6] rel. viscosity in $CH_2Cl_2$, 25° C., 0.5 g/100 ml
[7] $M_\eta$ is the molecular weight calculated from $\eta_{rel}$
[8] Calibration from: G.V. Schultz, A. Horbach, Markomol. Chem. 29 93 (1959) osmometrically determined number average molecular weights determined according to paragraph 3.
[9] X = number of end groups per molecule The polycarbonates according to the invention have an increased glass temperature in comparison with linear polycarbonates with comparable weight average molecular weights, as measured by differential thermoanalysis. Furthermore, the polycarbonates according to the invention have melting properties (apparent melting viscosity as a function of the shear rate), which are comparable to the branched polycarbonate.

As is customary, additives of all kinds can be added to the polycarbonates according to the invention, during or after the production process. In this connection, the following may be mentioned: dyestuffs, pigments, mold release agents, stabilizers against the effects of moisture, heat and UV, lubricants, fillers, such as glass powder, quartz products, graphite, molybdenum sulphide, metal powder, powders of higher-melting plastics, e.g. polytetrafluoroethylene powder, natural fibres, such as cotton, sisal and asbestos, furthermore glass fibres of the most varied kinds, metal filaments as well as, fibres which are stable during the time of contact with the melt of polycarbonate and which do not noticeably damage the polycarbonates.

The polycarbonates according to the invention are suitable for processing by extrusion and injection moulding as well as for film production. Owing to the outstanding stiffening properties of the melt strip, they are also suitable for the production of hollow mouldings according to the blow-moulding process. The excellent structurally viscous properties make it possible, for example, to produce extrusion films with good mechanical properties.

By means of injection moulding, mouldings of all kinds, such as casing sections, coverings as well as parts for the electrical sector and for household appliances of all kinds, can be produced without difficulty.

Experimental section

Preparation of bisphenol A bischlorocarboxylic acid ester. 228 g of 4,4'-dihydroxydiphenol-2,2-propane (bisphenol A) are suspended in 1170 g toluene in a dry apparatus. Then, while stirring and under nitrogen atmosphere and at −5° to 0° C., 297 g (207 ml) of phosgene are added. Then the mixture is cooled to −20° C. and a solution of 242 g N,N-dimethylaniline in 242 g of toluene is added dropwise and stirring is continued for 30 min.) at −20° C. After slowly heating to room temperature the mixture is further heated to 85°–90° C. The reaction solution is kept for 30 minutes at this temperature, during which excess phosgene is evaporated and the hydrochloride melts. Then the mixture is cooled to 20° C., the hydrochloride being precipitated in crystalline form or in the form of thick oil. After washing twice with 5% HCl (approx. 15° C.) and washing three times with water (also 15° C.) the organic phase is dried over sodium sulphate and filtered. Toluene is distilled off at 90° C. and 100 mm Hg and later at 90° C. and 15 mm Hg. The residue can be distilled at 195°–200° C. and 0.2 mm Hg and purified, m.p. 95° C.

EXAMPLE 1 (Comparative example)

Production of a polycarbonate according to the known interfacial process $\eta$rel: 1.29–1.30 $M_{LS}$=32,000

Approximately 454 parts of 4,4'-dihydroxdiphenyl-2,2-propane and 5.95 parts of phenol are suspended in 1.5 l water. The oxygen is removed from the reaction mixture in a 3-necked flask equipped with a stirrer and gas inlet, by passing nitrogen through the reaction mixture for 15 minutes while stirring. Then 355 parts of a 45% sodium hydroxide solution and 1000 parts of methylene chloride are added. The mixture is cooled to 25° C.

By maintaining this temperature by cooling, 237 parts of phosgene are added over a period of 120 minutes. An additional amount of 75 parts of a 45% sodium hydroxide solution is added after 15–30 minutes or after the phosgene absorption has begun. A highly viscous solution is obtained, whose viscosity is regulated by the addition of methylene chloride. The aqueous phase is separated off. The organic phase is washed with water until free of salt and alkali. The polycarbonate is isolated from the washed solution and dried. The polycarbonate has a relative viscosity of 1.29–1.30, measured in a 0.5% strength solution of methylene chloride at 25° C. This corresponds approximately to a molecular weight of $M_{LS}$ 32,000.

EXAMPLE 2

A solution of 40.4 g (0.40 mol) of triethylamine in 2000 ml water is initially introduced into a reaction vessel. Then a solution of 142.4 g (0.40 mol) diphenol-A-bischlorocarboxylic acid in 2000 ml of freshly distilled methylene chloride is added while stirring at 25° C. (cool with ice) over 15 minutes.

After 30 minutes the methylene chloride phase is separated off and washed once with an approx. 5% aqueous NaOH, twice with an approx. 10% phosphoric acid and with water until neutral and free of salt. The organic phase is filtered and precipitated with ligroin. The precipitated product is dried over night at 80° C. under a water pump vacuum. The product has a relative solution viscosity of 1.40 and a molecular weight of $M_{LS}$ 57,000.

EXAMPLE 3

A solution of 24 g NaOH (0.6 mol) and 3.5 g triethylamine (0.035 mol) in 1 l water is initially introduced into a reaction vessel. Then 35.3 g of bisphenol-A-bischlorocarboxylic acid ester, dissolved in 1 l of alcohol-free methylene chloride are added while stirring at 25°

C. (cool with ice) over 1.5 minutes. After 30 minutes the methylene chloride phase is separated off and washed successively with dilute NaOH, dilute phosporic acid and distilled water until neutral and free of salt. The organic phase is filtered and precipitated in ligroin. The precipitated product is dried for 48 hours at 80° C. under a water pump vacuum. The product has a relative solution viscosity of $\eta rel = 1.373$ and a molecular weight of $M_{LS} = 50,000$.

EXAMPLES 4 and 5

Examples 4 and 5 are produced in the same way as the method described in Example 2. The variable can be taken from the following table:

| Ex. | Mols of triethyl amine | Mols of bischoro- carboxylic acid ester | Reaction temp. °C. | End groups per mol | $\eta_{rel}$ | $M_{LS}$ |
|---|---|---|---|---|---|---|
| 2 | 0,400 | 0,40 | 25 | 0,05 | 1,40 | 57.000 |
| 3 | 0,035 | 0,10 | 25 | 0,99 | 1,37 | 50.000 |
| 4 | 0,300 | 0,40 | 25 | 0,09 | 1,30 | 42.000 |
| 5 | 0,800 | 0,40 | 20 | 0,07 | 1,32 | 46.000 |

The polycarbonate of the comparative example has a relative solution viscosity of 1.30, a $M_{LS}$ molecular weight of 32,000 and 1.95 end groups per molecule including taking into account the phenyl end groups (see analytical section 2.3).

EXAMPLE 6

A solution of 61.6 g of bisphenol A (0.27 mol), 1.20 g NaOH (3 mols) as well as 101 g concentrated triethylamine (1.0 mol) in 3000 ml water are initially introduced into a reaction vessel. Then a solution of 142.4 g of bisphenol A bischlorocarboxylic acid ester (0.40 mol) in freshly distilled methylene chloride are added, while stirring, at 20° C. (cool with ice) over 15 minutes.

After stirring has been continued for 30 minutes, the methylene chloride phase is separated off and washed once with an approx. 5% aqueous NaOH, twice with an approx. 10% phosphoric acid and with water until neutral and free of salt. The organic phase is filtered and precipitated with ligroin. The precipitated product is dried over night at 80° C. under a water pump vacuum.

The product had a relative solution viscosity 1.41 and a molecular weight of $M_{LS} = 53,000$.

EXAMPLES 7 and 8

Examples 7 and 8 are produced according to the method described in Example 6. The variables are to be taken from the following table:

| Ex. | Mols of NaOH | Mols of triethyl- amine | Mols of bisphenol bischloro- carboxylic acid ester | Mols of bisphenol A | Reaction temp. | End groups per mol | $\eta_{rel}$ | $M_{LS}$ |
|---|---|---|---|---|---|---|---|---|
| 6 | 3 | 1,0 | 0,4 | 0,27 | 20 | 0,7 | 1,41 | 53.000 |
| 7 | 3,3 | 2,0 | 0,4 | 0,20 | 25 | 0,5 | 1,29 | 39.000 |
| 8 | 2,8 | 1,0 | 0,4 | 0,05 | 25 | 0,35 | 1,34 | 48.000 |

We claim:

1. Polycarbonates incorporating residues of diphenols of the formula (I)

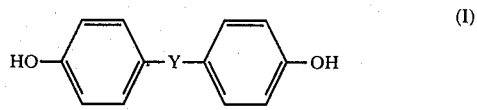

in which

Y denotes a single bond, an alkylene or alkylidene radical with 1-7 C atoms, a cycloalkylene or cycloalkylidene radical with 5-2 C atoms, —O—, —S—,

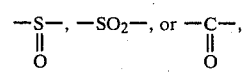

which have weight average molecular weights $M_{LS}$, measured by light scattering, of at least 15,000, which are characterised in that the polycarbonates exhibit on average 0 to 1.5 mols end groups per mol polycarbonate.

2. Polycarbonates according to claim 1, characterised in that the polycarbonates contain, on the average, 0.3 to 1.0 mols end groups per mol polycarbonate.

3. Polycarbonates according to claim 1, characterised in that the polycarbonates contain, on the average, 0.3 to 0.8 mols end groups per mol polycarbonate.

4. Polycarbonates according to claim 1, 2 or 3, incorporating residues of 2,2-bis-(4-hydroxyphenyl)-propane.

5. Moldings and films comprising the polycarbonate of claim 1, 2 or 3.

* * * * *